United States Patent [19]

Tracy et al.

[11] 4,113,954

[45] Sep. 12, 1978

[54] PROCESS FOR THE PREPARATION OF 3-ANILINO-5-PYRAZOLONES

[75] Inventors: David J. Tracy, Lincoln Park, N.J.; Walter F. Hoffstadt, Vestal, N.Y.

[73] Assignee: GAF Corporation, New York, N.Y.

[21] Appl. No.: 742,058

[22] Filed: Nov. 15, 1976

Related U.S. Application Data

[63] Continuation-in-part of Ser. No. 603,533, Aug. 11, 1975, abandoned.

[51] Int. Cl.$^2$ ............................................ C07D 231/52
[52] U.S. Cl. ........................................ 548/365; 560/35
[58] Field of Search ................... 260/310 A, 471 A; 560/35; 548/365

[56] References Cited

U.S. PATENT DOCUMENTS

| | | | |
|---|---|---|---|
| 3,798,234 | 3/1974 | Meier et al. | 260/310 A |
| 3,979,412 | 9/1976 | Arai et al. | 260/310 A |

FOREIGN PATENT DOCUMENTS

| | | | |
|---|---|---|---|
| 1,134,329 | 2/1966 | United Kingdom | 260/310 A |

*Primary Examiner*—Natalie Trousof
*Assistant Examiner*—Jane T. Fan
*Attorney, Agent, or Firm*—Walter C. Kehm; Walter Katz

[57] ABSTRACT

In accordance with the present invention, it has been found that 3-anilino-5-pyrazolones can be prepared in high yields by a multi-step process using available starting materials. In the first step of the process, an alkyl $\beta$-alkoxy-$\beta$-iminopropionate salt is reacted with a suitable alkanol to form an orthoester intermediate in situ. The orthoester then is converted in high yields to the corresponding imidic ester by condensation with an aniline while simultaneously removing alkanol from the reaction mixture to drive the equilibrium reaction to completion. In a preferred form of the invention, formation of the imidic ester is carried out in a high boiling solvent whose presence enables the condensation to be carried out effectively at a high temperature, and which facilitates distillation of the more volatile alkanol by-product from the reaction mixture at atmospheric pressure.

17 Claims, No Drawings

PROCESS FOR THE PREPARATION OF 3-ANILINO-5-PYRAZOLONES

The application is a continuation-in-part of application Ser. No. 603,533, filed Aug. 11, 1975, now abandoned.

BACKGROUND OF THE INVENTION

This invention relates to an improved process for the preparation of 3-anilino-5-pyrazolones, which are important intermediates in the manufacture of photographic materials known in the art as magenta color formers.

DESCRIPTION OF THE PRIOR ART

The formation of colored photographic images by coupling an oxidized primary aromatic amine developing agent with a color former or coupling compound is well known. In these processes, certain pyrazolones, such as 2-pyrazolin-5-ones, are used as magenta color formers. These pyrazolones ordinarily are made from 3-anilino-5-pyrazolone intermediates.

There are presently a considerable number of methods known to the art for the preparation of 3-anilino-5-pyrazolones, but these are severely limited with respect to the substituents that can be placed in the anilino group, the yields obtainable, or the economy of the process. Representative of the state of the art are the U.S. Pat. Nos. 2,254,108, 2,983,608, 2,343,703, 3,615,506, and 3,798,234 and British Pat. Nos. 1,129,333, 1,129,334 and 1,134,329. The aforesaid U.S. patents, except No. 3,798,234, are particularly deficient with respect to the substituent groups which can be used, while said U.S. Pat. No. 3,798,234 and the British patents suffer the disadvantage of relatively poor yields or economy of manufacture of the desired pyrazolones. Accordingly, it is an object of the present invention to provide an improved process for the preparation of 3-anilino-5-pyrazolones in high yields.

SUMMARY OF THE INVENTION

In accordance with the present invention, it has been found that 3-anilino-5-pyrazolones having desired substituent groups therein can be prepared in high yields by a multi-step process using available starting materials. In the first step of the process, an alkyl β-alkoxy-β-iminopropionate salt is reacted with a suitable alkanol to form an orthoester intermediate in situ. The orthoester then is converted in high yields to the corresponding imidic ester by condensation with an aniline while simultaneously removing alkanol from the reaction mixture to drive the equilibrium reaction to completion. In a preferred form of the invention, the formation of the imidic ester is carried out in a high boiling solvent whose presence enables the condensation to be carried out more effectively at a high temperature than with alkanol alone. Particularly, the high boiling solvent mixture adds volume to the reaction mixture which enables good agitation of the reactants at a predetermined and measureable reaction temperature. Furthermore, it facilitates the simultaneous distillation of the more volatile alkanol by-product from the reaction mixture.

After filtering to remove the solid ammonium halide by-product of the reaction, the resulting imidic ester solution is reacted with a hydrazine to form an imidine compound, which is then cyclized to provide the desired 3-anilino-5-pyrazolone. This sequence of steps, in combination, provides the useful pyrazolones in high yields and in relatively low cost. A particular feature of the process of the invention is that no isolation of intermediates or change of solvent is necessary during the several steps of the process.

DESCRIPTION OF THE PREFERRED EMBODIMENTS

The 3-anilino-5-pyrazolones produced herein by the improved process of the invention have the general formula:

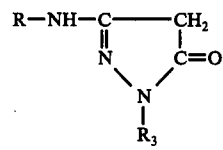

where R and $R_3$ are selected from the group consisting of phenyl and phenyl substituted with one or more substituents selected from the group consisting of halo, nitro and alkoxy, and combinations thereof, being the same or different.

Suitable R and $R_3$ groups include phenyl; a nitrophenyl, such as 4-nitrophenyl and 3-nitrophenyl; a halophenyl, such as 2-chlorophenyl, 2-bromophenyl, 2,6-dichlorophenyl, 2,4,5-trichlorophenyl, 2,4,6-trichlorophenyl, 3,5-dibromophenyl and 4-fluorophenyl; and alkoxy phenyl, such as 2-ethoxyphenyl and 4-butoxyphenyl; and combinations thereof, such as 2,6-dichloro-4-methoxyphenyl, 2-chloro-5-nitrophenyl 2,6-dichloro-4-nitrophenyl and 2-chloro-4-nitrophenyl.

In a preferred embodiment of the invention, at least one of R and $R_3$, preferably R, is a phenyl group substituted with a halo and a nitro group, which is particularly useful in making the 2-pyrazolin-5-one color formers.

A suitable starting material for the process of the invention is an alkyl β-alkoxy-β iminopropionate salt having the general formula:

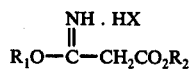

where
$R_1$ and $R_2$ are lower alkyl, which may be same or different, and
X is a halogen;

which may be prepared by the reaction of the corresponding nitrile with an appropriate alkanol and hydrogen halide, as described in Ber. 87, 205 (1954). Ethyl-β-ethoxy-β-iminopripionate hydrogen chloride, for example, may be prepared by reaction of ethyl β-cyanopropionate, ethanol and hydrogen chloride.

In the first step of the process of the invention, the alkyl β-alkoxy-iminopropionate salt is contacted with a primary or secondary lower alkanol to form an orthoester intermediate in situ. The lower alkanol must be a non-hindered alkanol, that is, a primary or secondary lower alkanol (i.e. not a tertiary alkanol) so that the reaction between iminopropionate and alkanol can preceed satisfactorily to the orthoester stage. Both the lower alkanol and the alkoxy group of the iminopropionate may be selected from $C_1$–$C_4$ groups, which may be the same or different. Thus the three alkoxy groups of the resulting orthoester can be either all the same (e.g., trimethoxy, triethoxy, etc.) or else they can be different, depending upon the respective nature or identity of the alkoxy group and of the alkyl moiety of the alkanol reactant.

This reaction may be carried out in the alkanol reactant, which can then act as a solvent in the reaction, or, preferably, in a solvent admixture which includes a high boiling component, as will be described in detail hereinafter.

Reaction between the iminopropionate and alkanol is carried out at ambient temperatures, suitably at room temperature for about 12–24 hours.

Once the orthoester is formed in situ, it is directly converted to coresponding imidic ester by condensation with a suitable aniline. As a feature of the present invention, this reaction is carried out while simultaneously removing two moles of alkanol by-product from the reaction mixture, thereby providing the desired imidic ester in high yields, according to the following equations:

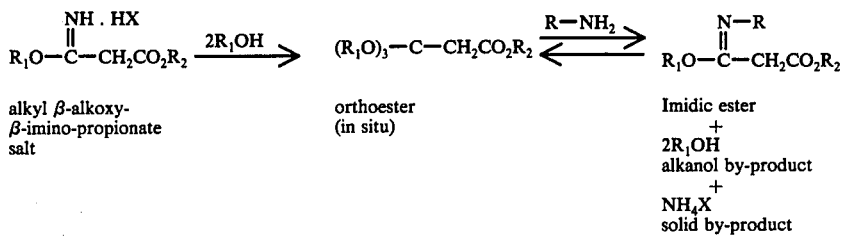

alkyl β-alkoxy-
β-imino-propionate
salt orthoester
(in situ)

Imidic ester
+
2R₁OH
alkanol by-product
+
NH₄X
solid by-product where
$R_1$ and $R_2$ are as previously defined, and
R is phenyl or phenyl substituted with one or more substituents selected from nitro, halo and alkoxy, and combinations thereof.

Removal of the alkanol by-product in the manner described drives the equilibrium reaction between orthoester and aniline to completion, thus substantially increasing the yield of the desired imidic ester.

As noted, condensation between the orthoester and the phenylamine preferably is carried out in the presence of a high boiling solvent for said reactants. The high boiling solvent enables the condensation reaction to proceed at an elevated temperature, and facilitates the removal of the lower boiling alkanol by-product by distillation at atmospheric pressure, thereby increasing the yield of imidic ester. Suitable high boiling solvents are those in which the reactants are inert and wholly miscible or soluble, and which have a boiling point higher than the alkanol itself, so as to enable the latter to be efficiently removed in the presence of the former. Typical solvents which satisfy these criteria have boiling points between about 80° C. and about 150° C., and are usually selected from among aromatic and aliphatic hydrocarbons and halogenated hydrocarbons, such as benzene, toluene, xylene, chlorobenzene, dichlorobenzene, tetrachloroethylene, tetrachloroethane and the like.

In a typical run, the imidic ester is formed advantageously by progressively heating the orthoester and phenylamine up to a reaction temperature of about 90°–120° C., while simultaneously removing two moles of the alkanol by-product by distillation at atmospheric pressure. Preferably, the reactants are heated up to about 110° C. during a period of about 3 or 4 hours, and then held at 110° C. for about ½ hour, during which heating periods alkanol is being distilled off continuously.

Of course, the high boiling solvent may be included initially in the charge of reactants which are used to form the orthoester, i.e., the iminopropionate and alkanol, and thus be ready for the next stage.

Solid ammonium halide, e.g., ammonium chloride, which is deposited during the course of the reaction as a by-product, then is filtered off to provide the imidic ester in the filtrate ready for the next step in the process.

Representative non-limiting examples of unsubstituted or substituted anilines suitable for use in the first step of the process include the following: aniline; o-, m-, or p-chloroaniline; o-, m-, or p-bromoaniline; o-, m-, or p-nitroaniline; 2,3-, 2,5-, 2,6-dibromoaniline; 2,3-, 2,4-, 2,5-, 2,6-, 3,4-, or 3,5-dichloroaniline; 2-chloro-4-nitroaniline; 2-chloro-5-nitroaniline; 4-chloro-2-nitroaniline; 4-chloro-3-nitroaniline; 2-methoxy-4-nitroaniline; 2-methoxy-5-nitroaniline; 4-methoxy-2-nitroaniline; 2,4-dinitroaniline; 2,6-dinitroaniline; 3,5-dinitroaniline; 2,5-dichloro-4-nitroaniline; 2,6-dichloro-4-nitroaniline; 4,5-dichloro-2-nitroaniline; 2,4,6-trichloroaniline; 4-fluoro-2-nitroaniline; and 4-fluoro-3-nitroaniline.

The imidic ester solution then is reacted with phenylhydrazine to form an amidine in accordance with the following equation:

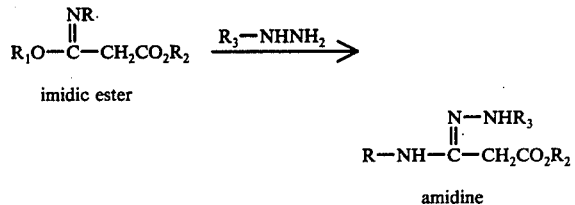

amidine where $R_3$ is phenyl or phenyl substituted with one or more of halo, nitro and alkoxy, and combinations thereof.

Accordingly, $R_3$ groups in the hydrazine reactant include phenyl; a halophenyl, e.g., 2-chlorophenyl, 2-bromophenyl, 2,6-dichlorophenyl, 2,4,5-trichlorophenyl, 2,4,6-trichlorophenyl, 3,5-dibromophenyl and 4-fluorophenyl; a nitrophenyl, e.g., 4-nitrophenyl and 3-nitrophenyl; and alkoxy, e.g., 2-ethoxyphenyl and 4-butoxyphenyl, and combinations thereof, such as: 2,6-dichloro-4-methoxyphenyl, 2-chloro-5-nitrophenyl, 2,6-dichloro-4-nitrophenyl and 2-chloro-4-nitrophenyl.

The amidines thus-prepared then are converted to the desired 3-anilino-5-pyrazolones by reaction with a cyclization agent which effects ring closure of the amidine. Suitably, from one to two molar equivalents of the cyclization agent is used for this purpose. The cyclization agent usually is a base, e.g. an alkali, an alkaline earth or a metal $C_1$–$C_5$ alkoxide.

Specific applications of the compositions and processes of the present invention and the various alternative embodiments thereof are further illustrated by the examples which follow. The specific details of these examples are not to be taken as limitations upon the invention.

EXAMPLE I 1-(2,4,6-trichlorophenyl)-3-(2-chloro-5-nitroanilino)-5-pyrazolone

A. Ethyl β-methoxy-β-(2-chloro-5-nitrophenylimino)propionate

To a 5 l. flask equipped with stirrer, condenser and and thermometer are charged 730 g. of ethyl β-ethoxy-β-iminopropionate hydrochloride, 386 g. of 2-chloro-5-nitroaniline, and 2500 ml. of anhydrous methanol. The mixture is stirred 16 hours at room temperature. Methanol then is distilled of at atmospheric pressure while heating the reaction mixture up to a temperature of 110° C., said temperature having held at 110° C. for ½ hour. The solid ammonium chloride formed then is filtered and the filter cake is washed well with methanol. The filtrate contains the desired imidic ester which is used directly in the next step.

B. Ethyl β-(2,4,6-trichlorophenylhydrazone)-β-(2-chloro-5-nitroanilino) propionate A total of 2500 ml. of methanol is added to the filtrate from A and then 439.5 g. of 2,4,6-trichlorophenylhydrazine. The mixture is refluxed for 16 hours and cooled to room temperature. The reaction product is a solution of the desired amidine.

C.

484 g. of 25% sodium methoxide solution is added to the filtrate from B. The mixture is refluxed for 1 hour and 130 ml. of glacial acetic acid is added to a pH of 7. The mixture is cooled to 5°–10° C., filtered, and washed with methanol. The solid is purified by reslurrying in methanol, yielding 280 g. (32%) of the desired pyrazolone product, having a melting point of 274°–8° C.

Anal. Calculated: Cl, 32.6%. Found: Cl, 32.34%.

The process of Example I is followed except that 500 ml. of toluene solvent is included in the charge in step A.

560 g. (65%) of the desired pyrazolone product is obtained having a melting point of 271°–5° C.

EXAMPLE II 1-(2,4,6-trichlorophenyl)-3-(3-nitroanilino)-5-pyrazolone

The process of Example I is followed using 146 g. of ethyl 3-ethoxy-3-iminopropionate hydrochloride, 62 g. of m-nitroaniline, 600 ml. of anhydrous methanol, 88 g. of 2,4,6-trichlorophenylhydrazine, and 96.8 g. of 25% sodium methoxide. The desired pyrazolone product, melting point 252°–5° C., is obtained in 31% yield.

Anal. Calculated: C, 45.08%; H, 2.27%; N, 14.02%; Cl, 26.61%. Found: C, 44.23%; H, 2.36%; N, 14.53%; Cl, 26.12%.

The process of Example II is followed except that 500 ml. of toluene solvent is included to the charge in step A. The resulting pyrazolone is obtained in about 60% yield.

EXAMPLE III 1-(2,6-Dichloro-4-nitrophenyl)-3-(2,4-dichloroanilino)-5-pyrazolone The process of Example I, with addition of toluene solvent, is followed using 2,4-dichloroaniline and 2,6-dichloro-4-nitrophenylhydrazine to provide the corresponding pyrazolone, m.p. 229°–231° C.

EXAMPLE IV 1-(2,4,6-Trichlorophenyl)-3-(4-nitroanilino)-5-pyrazolone

The process of Example I, with addition of toluene, is followed using 4-nitroaniline and 2,4,6-trichlorophenylhydrazine to provide the corresponding pyrazolone, m.p. 300°–302° C.

EXAMPLE V

1-Phenyl-3-(2-chloro-4-nitroanilino)-5-pyrazolone

The process of Example I, with addition of toluene, is followed using 2-chloro-4-nitroaniline and phenylhydrazine to provide the corresponding pyrazolone, m.p. 245°–8° C.

It should be understood from the foregoing that the above description is merely illustrative of the preferred embodiments and specific examples of the present invention and that in all of which embodiments and examples, variations, such as, e.g., those previously described, can be made by those skilled in the art without departing from the spirit and purview thereof, the invention being defined by the following claims.

What is claimed is:

1. A process for the preparation of 3-anilino-5-pyrazolones comprising the steps of:
    (a) combining a lower alkyl β-lower alkoxy-β-iminopropionate salt with a primary or secondary lower alkanol and an aniline or an aniline substituted with one or more substituents selected from the group consisting of nitro, halo and alkoxy, and combination thereof in a high boiling point solvent which has a boiling point above that of the alkanol by-product of the process and forming therefrom an orthoester in situ,
    (b) heating while simultaneously removing the alkanol by-product from the reaction mixture containing said orthoester thereby to form an imidic ester,
    (c) filtering the reaction mixture of (b) to remove the solid ammonium halide formed during the reaction.
    (d) reacting said imidic ester in the filtrate with a phenylhydrazine selected from the group consisting of phenylhydrazine and a phenylhydrazine in which the phenyl group is substituted with one or more substituents selected from the group consisting of nitro, halo, and alkoxy, and combinations thereof, to form the corresponding amidine, and,
    (e) contacting said amidine with a cyclization agent to effect ring closure thereby to form said desired product.

2. A process according to claim 1 wherein said alkanol is removed by distillation at atmospheric pressure.

3. A process according to claim 1 wherein said boiling point of said high boiling solvent is between about 80° C. and about 150° C.

4. A process according to claim 1 wherein said heating of said reactants is carried out by progressively increasing the reaction temperature up to about 90°–120° C.

5. A process according to claim 1 wherein said lower alkyl group is methyl or ethyl and said lower alkanol is methanol or ethanol.

6. A process according to claim 3 wherein said high boiling solvent is selected from the group consisting of aromatic and aliphatic hydrocarbons and halogenated hydrocarbons.

7. A process according to claim 1 wherein said high boiling solvent is selected from the group consisting of benzene, toluene, xylene, chlorobenzene, dichlorobenzene, tetrachloroethylene and tetrachloroethane.

8. A process according to claim 1 in which at least one of said substituted aniline and said substituted phenylhydrazine contains a nitro substituent.

9. A process according to claim 1 wherein said substituted aniline is a nitroaniline.

10. A process according to claim 1 wherein said substituted phenylhydrazine is a halophenyl substituted hydrazine.

11. A process according to claim 1 wherein said substituted phenylamine is 2-chloro-5-nitroaniline, and said substituted phenylhydrazine is 2,4,6-trichlorophenylhydrazine.

12. A process according to claim 1 in which there is present excess lower alkanol thereby forming a solvent admixture with said high boiling solvent.

13. A process according to claim 1 in which both said lower alkyl group and said lower alkanol have the same alkyl group.

14. A process according to claim 1 wherein said substituted phenylhydrazine is a trihalophenylhydrazine.

15. A process according to claim 1 wherein said aniline is a halonitroaniline.

16. A process according to claim 1 wherein additional lower alkanol is added to said imidic ester filtrate to form a solvent admixture during reaction with said phenylhydrazine.

17. A process according to claim 1 wherein said high boiling solvent is included with said lower alkanol during formation of said orthoester intermediate.

* * * * *